(12) United States Patent
Castellano

(10) Patent No.: US 6,613,011 B2
(45) Date of Patent: Sep. 2, 2003

(54) GAS-PRESSURED ENGINE WITH VALVE

(75) Inventor: Thomas P Castellano, Santa Monica, CA (US)

(73) Assignee: Penjet Corporation, Santa Monica, CA (US)

(*) Notice: Subject to any disclaimer, the term of this patent is extended or adjusted under 35 U.S.C. 154(b) by 0 days.

(21) Appl. No.: 10/099,846

(22) Filed: Mar. 15, 2002

(65) Prior Publication Data

US 2002/0151841 A1 Oct. 17, 2002

Related U.S. Application Data

(63) Continuation-in-part of application No. 09/834,476, filed on Apr. 13, 2001.

(51) Int. Cl.⁷ .......................... A61M 5/30; F16K 51/00; F16L 29/00; F16L 37/28
(52) U.S. Cl. .................. 604/68; 604/69; 604/71; 251/149.1; 251/149.6
(58) Field of Search ............... 128/200.14, 200.21, 128/200.23; 604/68, 70, 140, 143; 251/149.6, 149.1; 222/394, 402.1; 137/557, 559; 116/266, 272; 141/2, 3, 4, 18, 21, 26, 27, 28

(56) References Cited

U.S. PATENT DOCUMENTS

| | | |
|---|---|---|
| 1,997,129 A | 4/1935 | Taylor et al. |
| 2,221,739 A | 11/1940 | Reiter |
| 2,605,763 A | 8/1952 | Smoot |
| 2,632,445 A | 3/1953 | Kas, Sr. |
| 2,642,062 A | 6/1953 | May |
| 2,680,439 A | 6/1954 | Sutermeister |
| 2,695,023 A | 11/1954 | Brown |
| 2,718,299 A | 9/1955 | Atwater et al. |
| 2,754,818 A | 7/1956 | Scherer |
| 3,110,310 A | 11/1963 | Cislak |
| 3,131,692 A | 5/1964 | Love |
| 3,141,583 A | 7/1964 | Mapel et al. |
| 3,293,749 A | 12/1966 | George et al. |
| 3,348,545 A | 10/1967 | Sarnoff et al. |
| 3,481,510 A | 12/1969 | Allen |
| 3,507,276 A | 4/1970 | Burgess |
| 3,517,668 A | 6/1970 | Brickson |
| 3,557,784 A | 1/1971 | Shields |
| 3,568,736 A | 3/1971 | Linch et al. |

(List continued on next page.)

FOREIGN PATENT DOCUMENTS

| | | |
|---|---|---|
| CA | 1103314 | 2/1978 |
| CA | 1258 019 | 8/1989 |
| CH | 293302 | 9/1953 |
| DE | 22140 | 4/1883 |
| DE | 730971 | 1/1943 |
| DE | 1070 784 | 6/1960 |
| DE | 1170436 | 11/1962 |
| EP | 0143 895 | 8/1964 |
| EP | 0037 696 | 3/1981 |
| EP | 0220 146 | 10/1986 |

(List continued on next page.)

*Primary Examiner*—Edward K. Look
*Assistant Examiner*—John K Fristoe, Jr.
(74) *Attorney, Agent, or Firm*—Pillsbury Winthrop LLP

(57) ABSTRACT

An engine with a valve suitable for containing compressed gas and expelling the same upon opening of the valve is provided. Upon application of sufficient force to an element of the valve, the compressed gas is released from the engine. In one embodiment, the engine is fitted with a reusable valve. In another embodiment, the engine includes an engine housing with a pop-out feature that indicates if the engine is critically overcharged. A method of implementing quality control schemes during the manufacture or production of the engine and its component parts is provided, as well as a method of filling the engine with a compressed gas.

79 Claims, 15 Drawing Sheets

U.S. PATENT DOCUMENTS

| | | | |
|---|---|---|---|
| 3,583,399 | A | 6/1971 | Ritsky |
| 3,688,765 | A | 9/1972 | Gasaway |
| 3,695,266 | A | 10/1972 | Lussier |
| 3,853,125 | A | 12/1974 | Clark et al. |
| 3,859,996 | A | 1/1975 | Mizzy et al. |
| 3,894,663 | A | 7/1975 | Carhart et al. |
| 3,977,574 | A | 8/1976 | Thomas |
| 4,022,207 | A | 5/1977 | Citrin |
| 4,031,892 | A | 6/1977 | Hurschman |
| 4,033,378 | A | 7/1977 | Pauliukonis |
| 4,099,548 | A | 7/1978 | Sturm et al. |
| 4,114,619 | A | 9/1978 | Wagner |
| 4,139,008 | A | 2/1979 | Wagner |
| 4,146,029 | A | 3/1979 | Ellinwood, Jr. |
| 4,169,474 | A | 10/1979 | Wagner |
| 4,284,077 | A | 8/1981 | Wagner |
| 4,333,458 | A | 6/1982 | Margulies et al. |
| 4,338,980 | A | 7/1982 | Schwebel et al. |
| 4,393,870 | A | 7/1983 | Wagner |
| 4,395,921 | A | 8/1983 | Oppenlander |
| 4,413,760 | A | 11/1983 | Paton |
| 4,415,101 | A | 11/1983 | Shapiro et al. |
| 4,425,121 | A | 1/1984 | Young et al. |
| 4,435,173 | A | 3/1984 | Siposs et al. |
| 4,444,560 | A | 4/1984 | Jacklich |
| 4,457,712 | A | 7/1984 | Dragan |
| 4,470,317 | A | 9/1984 | Sabloewski et al. |
| 4,471,802 | A | 9/1984 | Pryor |
| 4,475,905 | A | 10/1984 | Himmelstrup |
| 4,498,904 | A | 2/1985 | Turner et al. |
| 4,526,294 | A | 7/1985 | Hirschmann et al. |
| 4,529,401 | A | 7/1985 | Leslie et al. |
| 4,538,616 | A | 9/1985 | Rogoff |
| 4,573,970 | A | 3/1986 | Wagner |
| 4,581,022 | A | 4/1986 | Leonard et al. |
| 4,592,745 | A | 6/1986 | Rex et al. |
| 4,596,556 | A | 6/1986 | Morrow et al. |
| 4,600,403 | A | 7/1986 | Wagner |
| 4,613,328 | A | 9/1986 | Boyd |
| 4,659,327 | A | 4/1987 | Bennett et al. |
| 4,664,128 | A | 5/1987 | Lee |
| 4,676,781 | A | 6/1987 | Phillips et al. |
| 4,680,027 | A | 7/1987 | Parsons et al. |
| 4,710,172 | A | 12/1987 | Jacklich et al. |
| 4,710,178 | A | 12/1987 | Henri et al. |
| 4,722,728 | A | 2/1988 | Dixon |
| 4,743,229 | A | 5/1988 | Chu |
| 4,790,824 | A | 12/1988 | Morrow et al. |
| 4,820,287 | A | 4/1989 | Leonard |
| 4,834,149 | A | 5/1989 | Fournier et al. |
| 4,865,591 | A | 9/1989 | Sams |
| 4,874,367 | A | 10/1989 | Edwards |
| 4,883,472 | A | 11/1989 | Michel |
| 4,913,699 | A | 4/1990 | Parsons |
| 4,936,833 | A | 6/1990 | Sams |
| 4,941,880 | A | 7/1990 | Burns |
| 4,950,246 | A | 8/1990 | Muller |
| 4,959,056 | A | 9/1990 | Dombrowski et al. |
| 4,998,570 | A | 3/1991 | Strong |
| 5,009,634 | A | 4/1991 | Feldman et al. |
| 5,009,637 | A | 4/1991 | Newman et al. |
| 5,024,656 | A | 6/1991 | Gasaway et al. |
| 5,047,044 | A | 9/1991 | Smith et al. |
| 5,050,612 | A | 9/1991 | Matsumura |
| 5,064,413 | A | 11/1991 | McKinnon et al. |
| 5,069,668 | A | 12/1991 | Boydman |
| 5,085,642 | A | 2/1992 | Sarnoff et al. |
| 5,092,842 | A | 3/1992 | Bechtold et al. |
| 5,102,393 | A | 4/1992 | Sarnoff et al. |
| 5,104,380 | A | 4/1992 | Holman et al. |
| 5,112,317 | A | | 5/1992 | Michel |
| 5,114,406 | A | | 5/1992 | Gabriel et al. |
| 5,115,803 | A | * | 5/1992 | Sioutas ................ 128/200.23 |
| 5,139,484 | A | | 8/1992 | Hazon et al. |
| 5,180,371 | A | | 1/1993 | Spinello |
| 5,226,895 | A | | 7/1993 | Harris |
| 5,226,896 | A | | 7/1993 | Harris |
| 5,244,461 | A | | 9/1993 | Derlien |
| 5,244,465 | A | | 9/1993 | Michel |
| 5,249,584 | A | | 10/1993 | Karkar et al. |
| 5,254,100 | A | | 10/1993 | Huband |
| 5,256,157 | A | | 10/1993 | Samiotes et al. |
| 5,267,977 | A | | 12/1993 | Feeney, Jr. |
| 5,279,294 | A | | 1/1994 | Anderson et al. |
| 5,279,584 | A | | 1/1994 | Dillard, III et al. |
| 5,279,585 | A | | 1/1994 | Balkwill |
| 5,279,586 | A | | 1/1994 | Balkwill |
| 5,330,430 | A | | 7/1994 | Sullivan |
| 5,342,309 | A | | 8/1994 | Hausser |
| 5,354,287 | A | | 10/1994 | Wacks |
| 5,383,865 | A | | 1/1995 | Michel |
| 5,425,716 | A | | 6/1995 | Kawasaki et al. |
| 5,429,602 | A | | 7/1995 | Hauser |
| 5,445,620 | A | | 8/1995 | Haber et al. |
| 5,480,381 | A | | 1/1996 | Weston |
| 5,499,972 | A | | 3/1996 | Parsons |
| 5,503,627 | A | | 4/1996 | McKinnon et al. |
| 5,509,905 | A | | 4/1996 | Michel |
| 5,520,639 | A | | 5/1996 | Peterson et al. |
| 5,536,249 | A | | 7/1996 | Castellano et al. |
| 5,540,664 | A | | 7/1996 | Wyrick |
| 5,569,189 | A | | 10/1996 | Parsons |
| 5,593,388 | A | | 1/1997 | Phillips |
| 5,593,390 | A | | 1/1997 | Castellano et al. |
| 5,630,796 | A | | 5/1997 | Bellhouse et al. |
| 5,649,912 | A | | 7/1997 | Peterson |
| 5,704,911 | A | | 1/1998 | Parsons |
| 5,713,873 | A | | 2/1998 | Jehle |
| 5,728,074 | A | | 3/1998 | Castellano et al. |
| 5,730,723 | A | | 3/1998 | Castellano et al. |
| 5,820,602 | A | | 10/1998 | Kovelman et al. |
| 5,851,198 | A | | 12/1998 | Castellano et al. |
| 5,891,085 | A | | 4/1999 | Lilley et al. |
| 5,891,086 | A | | 4/1999 | Weston |
| 5,891,092 | A | | 4/1999 | Castellano |
| 5,893,397 | A | | 4/1999 | Peterson et al. |
| 5,899,880 | A | | 5/1999 | Bellhouse et al. |
| 5,925,021 | A | | 7/1999 | Castellano et al. |
| 5,957,166 | A | | 9/1999 | Safabash |
| 5,957,886 | A | | 9/1999 | Weston |
| 5,993,412 | A | | 11/1999 | Deily et al. |
| 6,014,970 | A | * | 1/2000 | Ivri et al. ............... 128/200.14 |
| 6,063,053 | A | | 5/2000 | Castellano et al. |
| 6,080,130 | A | | 6/2000 | Castellano |
| 6,096,002 | A | | 8/2000 | Landau |
| 6,132,395 | A | | 10/2000 | Landau et al. |
| 6,135,979 | A | | 10/2000 | Weston |
| D434,323 | S | | 11/2000 | Pattison |
| 6,145,762 | A | | 11/2000 | Orloff et al. |
| 6,149,625 | A | | 11/2000 | Weston et al. |
| 6,156,008 | A | | 12/2000 | Castellano |
| 6,168,587 | B1 | | 1/2001 | Bellhouse et al. |
| 6,174,304 | B1 | | 1/2001 | Weston |
| 6,223,786 | B1 | | 5/2001 | Castellano |
| 6,302,160 | B2 | | 10/2001 | Castellano |
| 6,309,371 | B1 | | 10/2001 | Deboer et al. |
| 6,406,455 | B1 | | 6/2002 | Willis et al. |
| 6,427,682 | B1 | * | 8/2002 | Klimowicz et al. .... 128/200.14 |
| 6,431,168 | B1 | * | 8/2002 | Rand et al. ............ 128/200.14 |

FOREIGN PATENT DOCUMENTS

| | | |
|---|---|---|
| EP | 0295 917 | 6/1988 |
| EP | 0327 910 | 1/1989 |
| EP | 0347 190 | 6/1989 |
| EP | 0368 191 | 11/1989 |
| EP | 0416 975 | 8/1990 |
| EP | 0427 457 | 11/1990 |
| EP | 0997662 | 10/1998 |
| FR | 1445 659 | 10/1957 |
| FR | 1149 735 | 12/1957 |
| FR | 1170 312 | 1/1959 |
| FR | 1378829 | 11/1964 |
| FR | 78 05814 | 3/1978 |
| FR | 2557 445 | 12/1984 |
| FR | 2 749169 | 6/1996 |
| GB | 1099488 | 10/1965 |
| GB | 1225 495 | 6/1967 |
| GB | 1574 267 | 2/1978 |
| GB | 2109 690 | 2/1982 |
| WO | 85/02546 | 10/1984 |
| WO | 89/08469 | 3/1989 |
| WO | 92/13583 | 2/1992 |
| WO | 93/10838 | 11/1992 |
| WO | 95/03844 | 7/1994 |
| WO | 9529720 | 11/1995 |
| WO | 96/19252 | 12/1995 |
| WO | 96/28202 | 3/1996 |
| WO | 97/13537 | 10/1996 |
| WO | 97/25015 | 1/1997 |
| WO | 0064514 | 4/2000 |
| WO | 48654 | 8/2000 |

\* cited by examiner

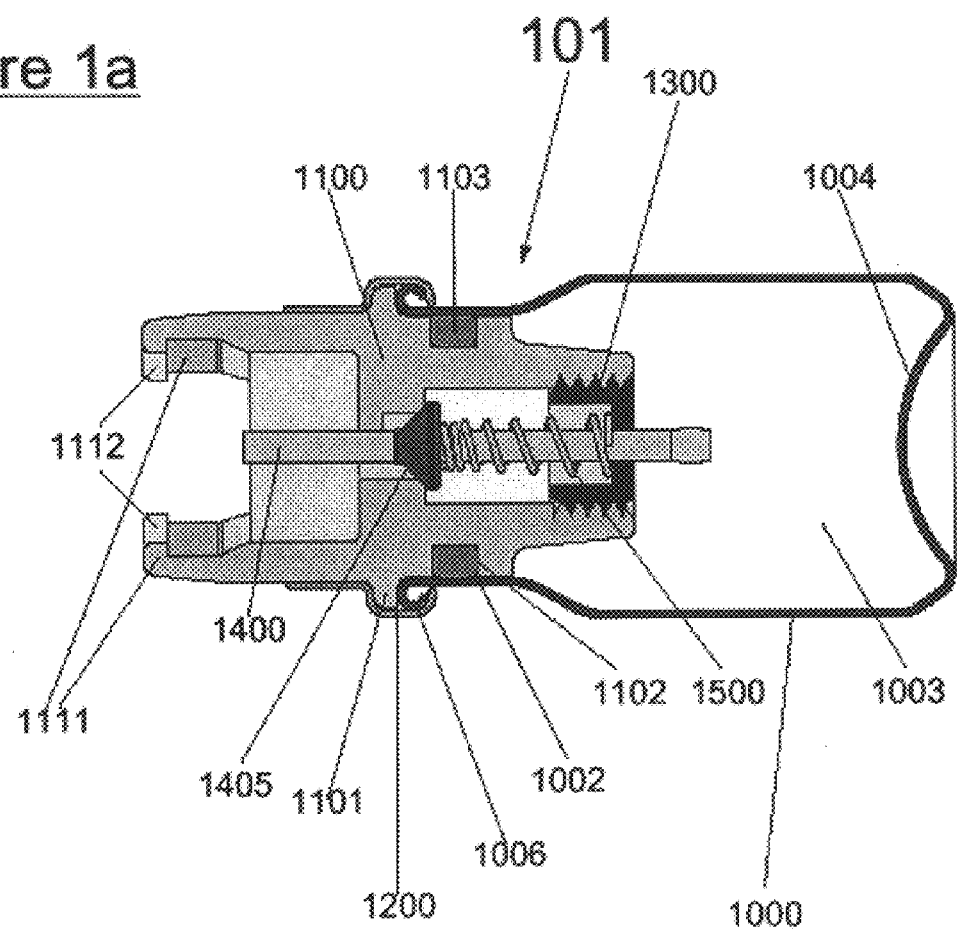

200      101

200   101

GAS-PRESSURED ENGINE WITH VALVE

RELATED APPLICATIONS

This is a Continuation-In-Part application of U.S. patent application Ser. No. 09/834,476 filed Apr. 13, 2001, which is incorporated by reference herein in its entirety.

FIELD OF THE INVENTION

This invention relates to an engine with a valve. More particularly, the invention relates to a gas-pressured engine with a valve.

BACKGROUND OF THE INVENTION:

Typically, needle-less medication injectors use either an expansion spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface.

In a jet injector, if the inert gas is not quickly and properly expelled, fluid may be improperly injected, as with those devices employing a compression spring. Conventional disposable needle-less injectors, such as those shown in U.S. Pat. No. 4,913,699 to Parsons and U.S. Pat. No. 5,009,637 to Newman et al. utilize a gas-containing, breakable tube that is shattered or cracked open by a side mounted trigger. Difficulties arise in the need to maintain tight tolerances on the breakable member, since minor changes in thickness can dramatically effect the pressure needed to deploy the gas from the gas chamber of the device. In addition, the broken shards of the breakable member are ejected at high speed when the gas is expelled and these shards can occasionally jam between the plunger driver and the housing, thereby preventing proper operation of the needle-less injector. Attempts to prevent small shards from being formed would obviate some of this potential, but tend to make activation of the device more difficult.

U.S. Pat. Nos. 6,080,130, 6,063,053, 5,851,198 and 5,730,723 describe needle-less injectors incorporating a gas power source, thus obviating some of the limitations inherent in compression spring injectors and addressing many of the concerns of conventional jet injectors. The injectors described therein have a pre-filled and self-contained compressed gas for providing pressure to inject medication into the skin surface of a patient without the use of a needle.

Gas power sources for needle-less injectors that employ either pop valves or breakaway tab valves to release the inert gas stored in their respective gas chambers, however, may only be opened once, thereby presenting difficulty with regard to quality control testing measures. Additionally, in filling a gas power source with compressed gas, safety measures and a range of quality control features are important. For instance, if a gas power source is critically overcharged, it may rupture during or after filling with a compressed gas. A rupture may occur in storage or even during operation (e.g., during the administration of a needle-less injection). Such an event may result in substantial injury to the recipient of an injection or to an individual administering the same. Other undesirable results may occur when the engine is used in conjunction with a device other than a needle-less injector, including harm to an individual or damage to a device to which such an engine is in operable contact.

SUMMARY OF THE DISCLOSURE

It is therefore an object of an embodiment of the instant invention to provide a gas-pressured engine that obviates, for practical purposes, the above-mentioned limitations.

In one embodiment of the instant invention, an engine includes an engine housing and a valve. Compressed gas may be contained in the engine housing, and released upon an opening of the valve. Further, the engine housing may include a depression on one end; the depression imparting to the engine a "pop-out" safety feature, wherein, when the engine is critically overcharged, the depression may substantially invert or otherwise deform its shape to provide greater internal volume for the compressed gas. This feature may avoid an engine rupture and may also provide an external visual cue that the engine is critically overcharged.

In another embodiment of the present invention, an engine is fitted with a reusable valve. The valve may contain a rubber head that is held against a fixed element of the engine such that depression of a trigger separates the head from the fixed element, releasing the compressed gas from the engine. A spring may be included in the valve to help maintain a proper airtight seal with the canister holding the compressed gas.

BRIEF DESCRIPTION OF THE DRAWINGS

FIGS. 1a–1c illustrates an engine with a valve in a closed position in accordance with an embodiment of the instant invention.

FIG. 1a illustrates a cross-sectional view.

FIG. 1b illustrates a proximate end perspective view.

FIG. 1c illustrates a cross-sectional view with a central axis.

FIG. 4a is a side perspective view,

FIG. 4b is a side cross-sectional view,

FIG. 4c is a proximate end perspective view and

FIG. 4d is a distal end perspective view.

FIG. 5a is a side perspective view,

FIG. 5b is a side cross-sectional view and

FIG. 5c is a proximate end perspective view.

FIG. 6a is a side perspective view,

FIG. 6b is a side cross-sectional view and

FIG. 6c is a proximate end perspective view.

FIG. 7a is a side perspective view in partial cross-section,

FIG. 7b is a side cross-sectional view,

FIG. 7c is a proximate end perspective view and

FIG. 7d is a distal end perspective view.

FIG. 8a is a side perspective view,

FIG. 8b is a side cross-sectional view prior to the distal end being shaped and

FIG. 8c is a proximate end perspective view.

FIG. 9a is a side perspective view in the relaxed state,

FIG. 9b is a side perspective view in the compressed state.

FIG. 10a is a side cross-sectional view of an engine with a valve in the closed position, the engine interacting with a device.

FIG. 10b is a side cross-sectional view of an engine with a valve in the open position, the engine interacting with a device.

DETAILED DESCRIPTION OF THE PREFERRED EMBODIMENTS

Figure 11:
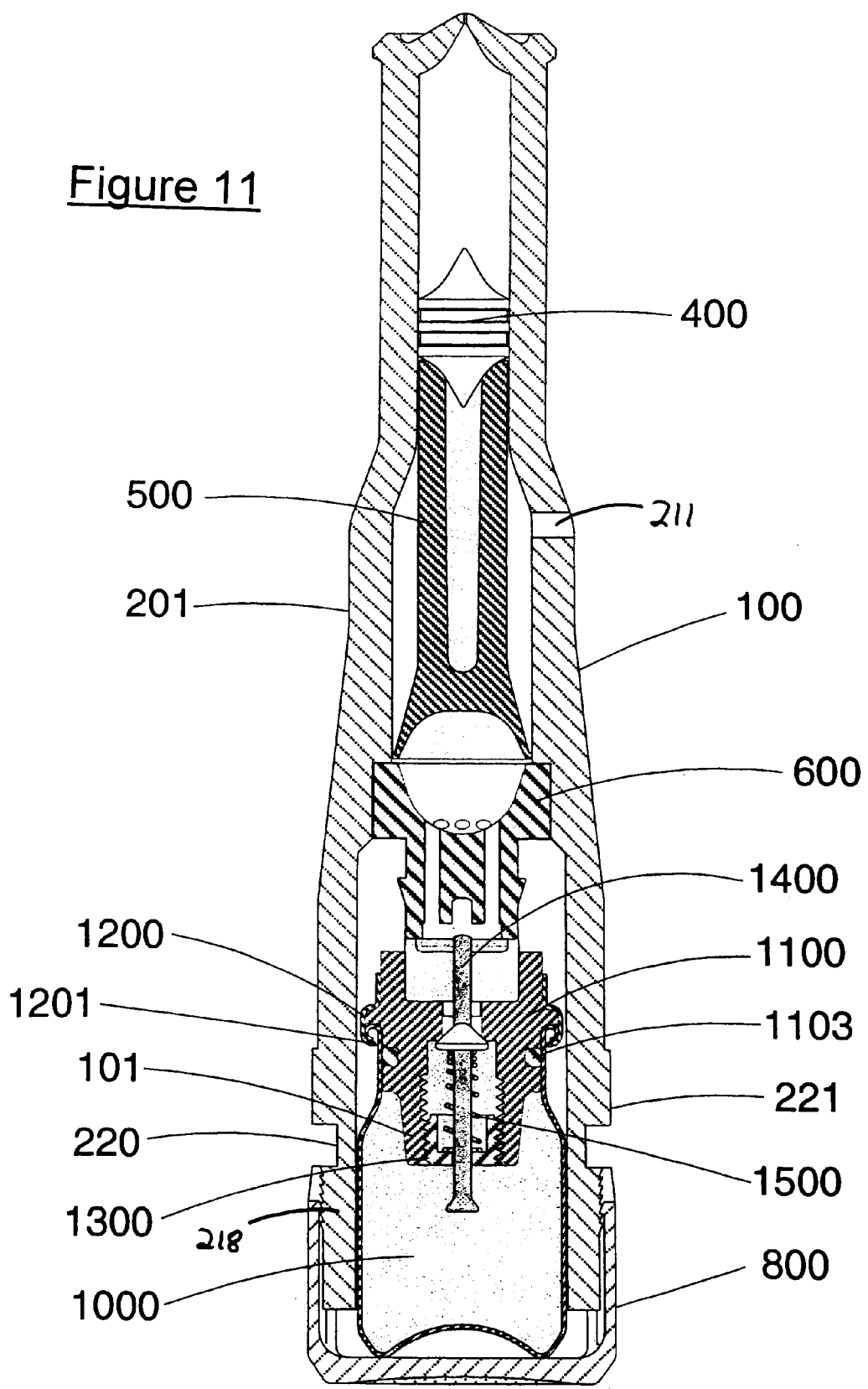
FIG. 11 illustrates a side, cross-sectional view of an engine with a valve interacting with a needle-less injector, in accordance with an embodiment of the instant invention.

As shown in the drawings for purposes of illustration, the invention is embodied in an engine with a valve. The engine may include various safety and quality control features, such as a pop-out feature that indicates if the engine is critically overcharged, and a valve that may be reused. The reusable valve allows an engine to be used more than once, and also provides a quality control feature in that the valve may be opened and closed prior to filling the engine with compressed gas. The engine and valve of the present invention may be used with a variety of devices, including, but not limited to, a needle-less injector (FIG. 11).

Figure 1B:
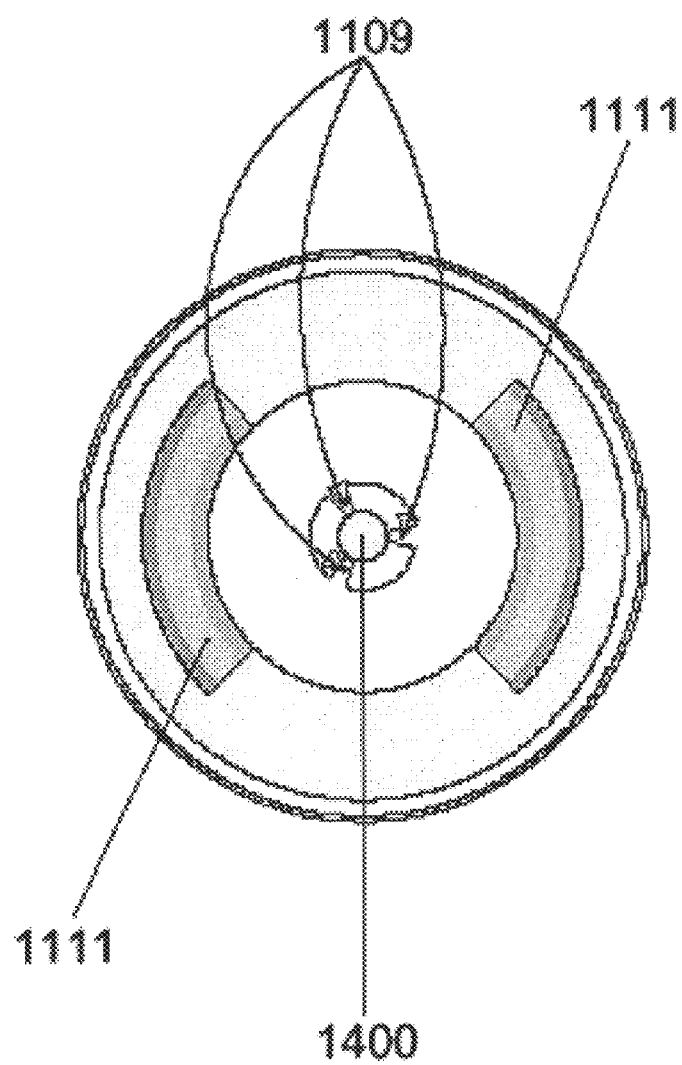
Figure 1C:
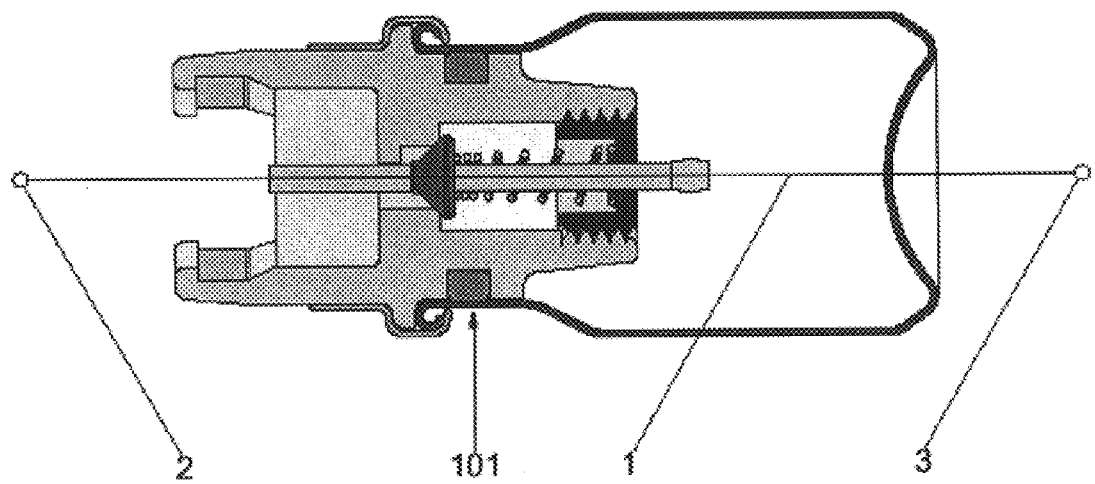

For ease in describing the various elements of the instant invention, the following spatial coordinate system will apply thereto. As depicted in FIG. 1c, a central axis 1 is defined through the length of a gas-pressured engine. This central axis has one terminus 2 at the proximate end of the engine, defined as that end of the device through which gas is expelled during normal operation of the engine. The other terminus 3 of the central axis is at the distal end of the engine, defined as that end of the device opposite the proximate end. Thus, various elements of the device of the instant invention may be described with reference to their respective proximate and distal portions, as well as their central axes.

An engine assembly 101 is provided in an embodiment of the present invention, as depicted in FIG. 1a. The engine assembly 101 may contain an engine housing 1000, as depicted in FIG. 4. The engine housing 1000 is preferably constructed of a material impermeable to a compressed gas stored therein, and has a hollow interior chamber 1003. Most preferably, the engine housing 1000 is comprised of stainless steel or a similar metal. A compressed inert gas is preferably stored within the engine housing 1000 prior to use. The most preferred gas is carbon dioxide, though other suitable gases may be employed, as well. In most preferred embodiments, the engine assembly 101 is overcharged (i.e., excess compressed gas is stored therein) to allow for use at variable altitudes without hampering its performance. This is to be distinguished from the instance in which the engine assembly is critically overcharged, which is the instance wherein the pressure inside the engine assembly is higher than a pressure threshold. An overcharged engine assembly may account for, e.g., variations in altitude, whereas a critically overcharged engine assembly presents a concern of engine rupture. An overcharged engine, as opposed to a critically overcharged engine, is preferred in accordance with an embodiment of the instant invention, as described above.

The engine housing 1000 is preferably roughly cylindrical in shape, though alternate configurations may be utilized. Referring to FIG. 4, the engine housing 1000 may have a portion of wide diameter 1001 and a portion of small diameter 1002, wherein the portion of small diameter 1002 is proximate to the portion of wide diameter 1001. The distal end of the engine housing 1000 may contain a circular depression 1004. The proximate end of the engine housing 1000 contains an opening 1005, and in preferred embodiments, a closing ridge 1006 encircles the opening 1005.

Figure 3:
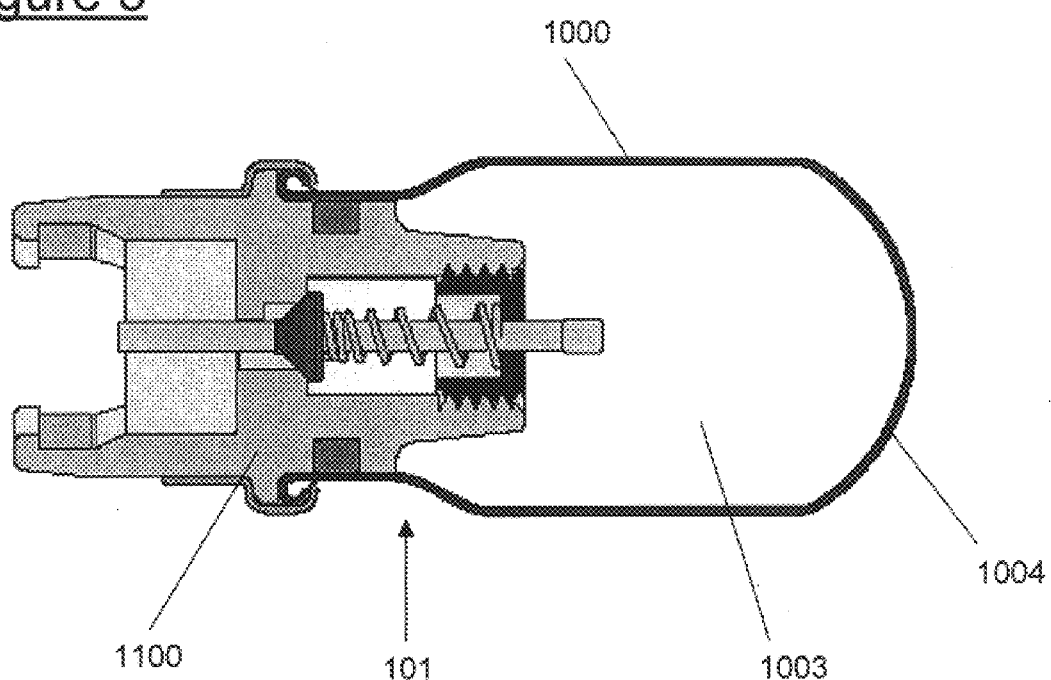
FIG. 3 illustrates a cross-sectional view of an engine with a valve in accordance with an embodiment of the instant invention. The engine housing includes a substantial deformation owing to it being critically overcharged.
Figure 4A:
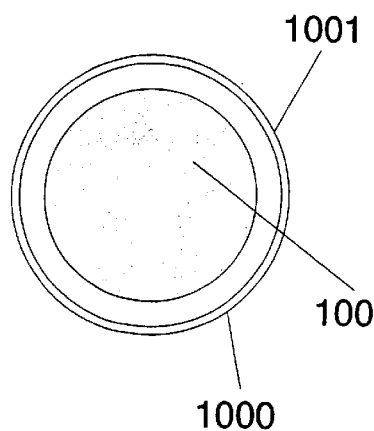
FIGS. 4a–d illustrate the engine housing of a needle-less injector in accordance with an embodiment of the instant invention.
Figure 4B:
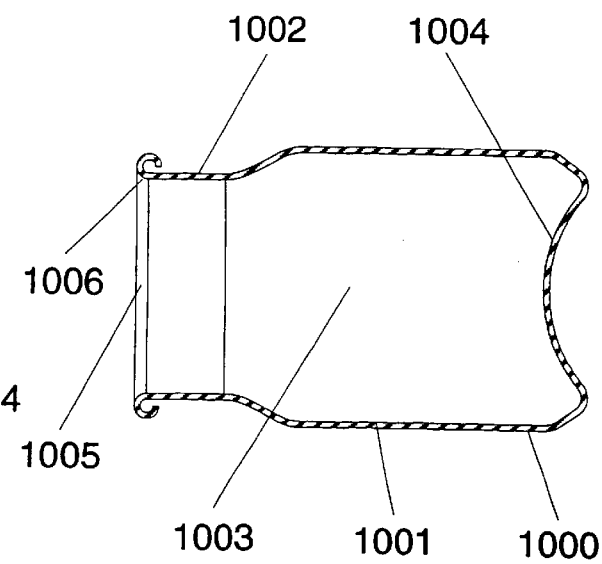
Figure 4C:
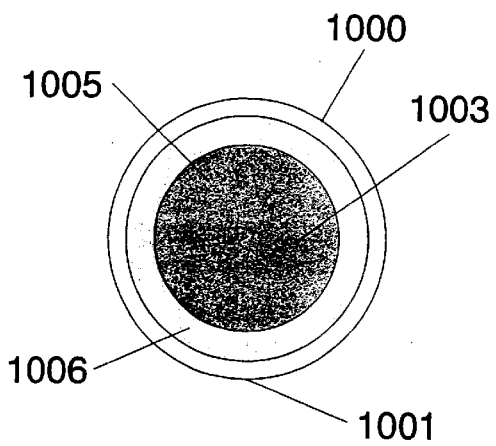
Figure 4D:
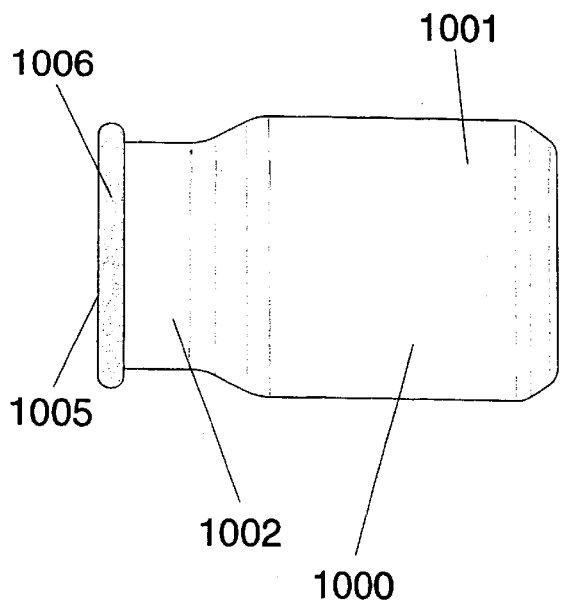

The circular depression 1004 that may be included in the engine housing 1000 in an embodiment of the present invention may impart a "pop-out" safety feature to the engine. As noted above, an overcharged engine is preferred in an embodiment of the present invention, while a critically overcharged engine may present safety concerns. Therefore, in a preferred embodiment of the present invention, as depicted in FIG. 3, the circular depression 1004 may substantially deform when the engine is critically overcharged (i.e., the internal pressure of the engine assembly is greater than a pressure threshold).

In a deformed state, the circular depression 1004 may take on any number of geometric configurations depending on, for example, impurities latent in the material used to form the engine housing or the magnitude of the overcharging. Thus, the substantially inverted configuration of the circular depression illustratively depicted in FIG. 3 is just one of a variety of potential configurations. By way of example, deformed configurations of the circular depression 1004 may be symmetrical or asymmetrical; may be centered about the central axis or disposed at a distance therefrom; or may include multiple deformations. Any such configuration may provide an external, visual indication that the engine is critically overcharged.

Figure 5A:
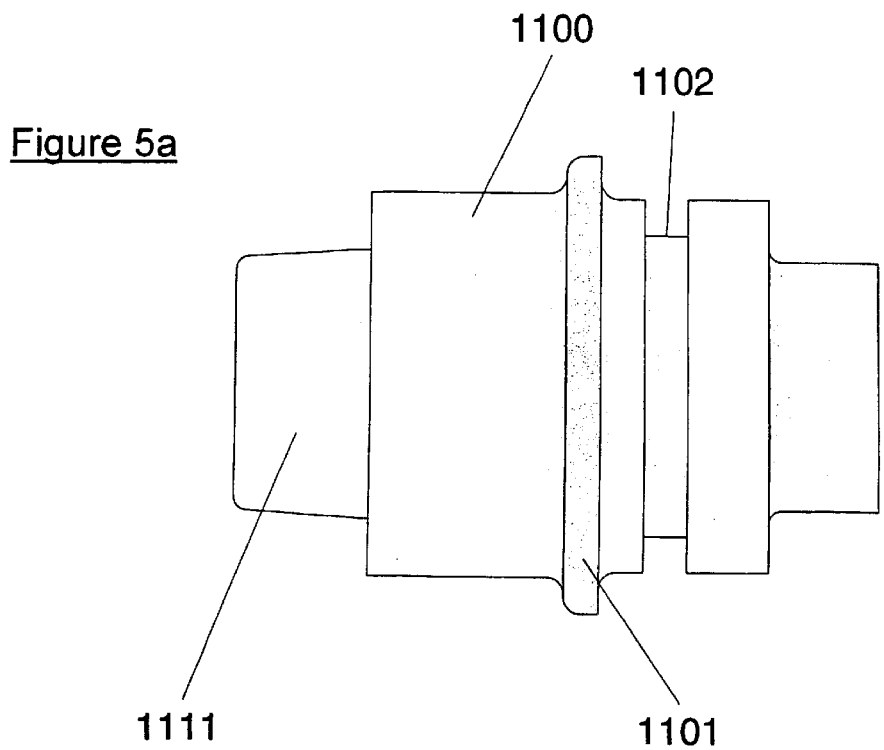
FIGS. 5a–c illustrate the valve body of a needle-less injector in accordance with an embodiment of the instant invention.
Figure 5B:
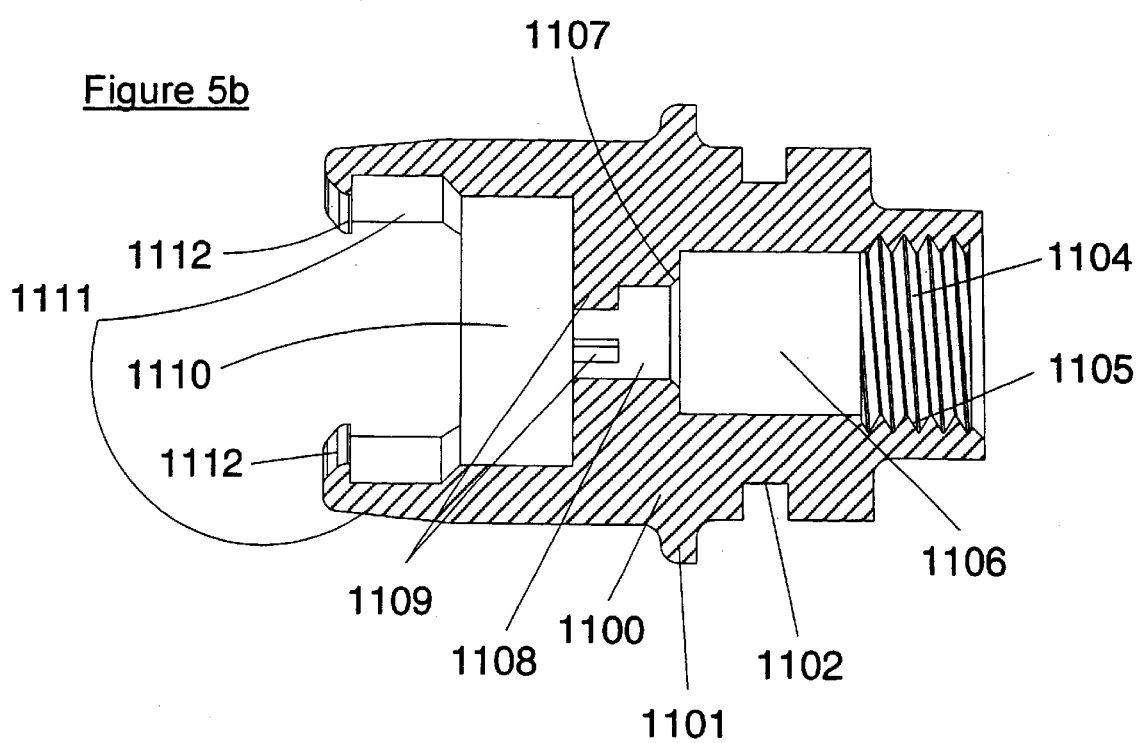
Figure 5C:
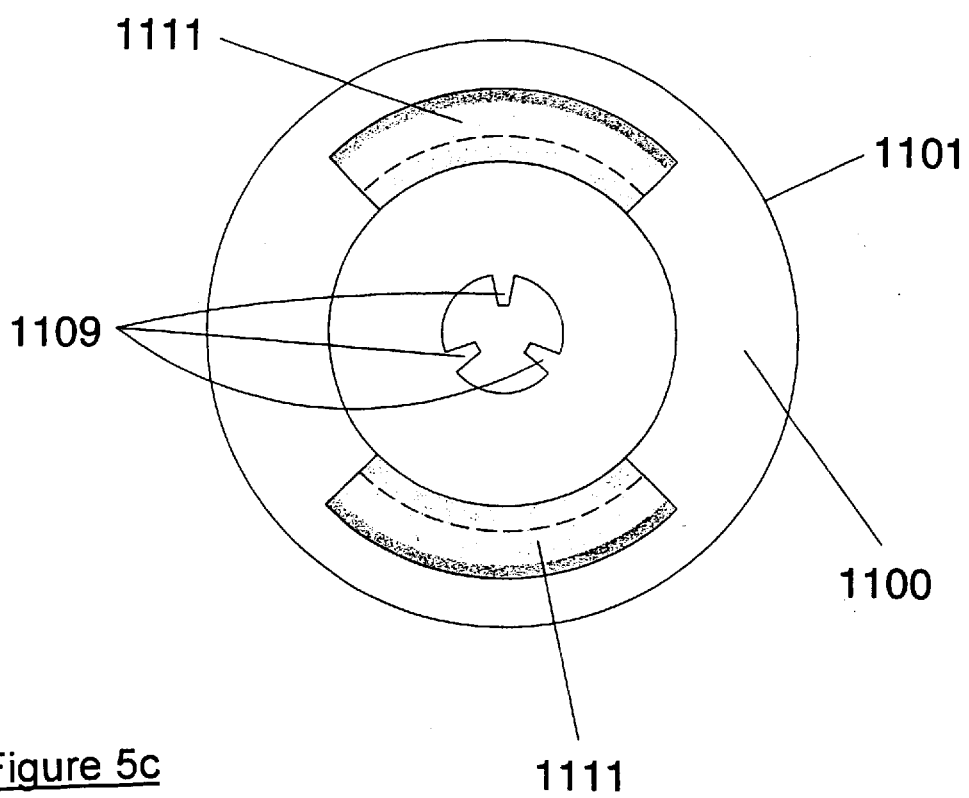

The engine assembly 101 preferably further contains a valve body 1100, as depicted in FIG. 5. The valve body 1100 is preferably roughly cylindrical in its overall shape, and more preferably resides at least partially within the engine housing 1000. The valve body 1100 most preferably has a closing rim 1101 around its outer circumference that rests against the closing ridge 1006 encircling the opening 1005 of the proximate end of the engine housing 1000. Most preferably, a closing ferrule 1200 is wrapped around both the closing rim 1101 and closing ridge 1006 to secure the valve body 1100 and engine housing 1000 to one another (see FIG. 1a).

In a most preferred embodiment of the present invention, as depicted in FIG. 1a, the exterior surface of the valve body

1100 distal to the closing rim 1101 is cylindrical and substantially corresponds to a preferred cylindrical interior surface of the engine housing 1000 along the portion of small diameter 1002. Most preferably, the small diameter of the engine housing 1000 is equal to or slightly greater than the diameter of the exterior surface of the valve body 1100, thereby allowing the valve body 1100 to reside at least partially within the portion of small diameter 1002.

Figure 6A:
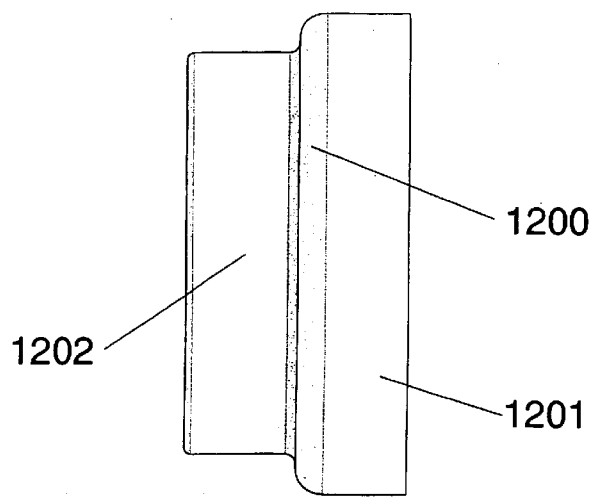
FIGS. 6a–c illustrate the closing ferrule of a needle-less injector in accordance with an embodiment of the instant invention, prior to the closing ferrule being mechanically fitted around a valve body and an engine housing.
Figure 6B:
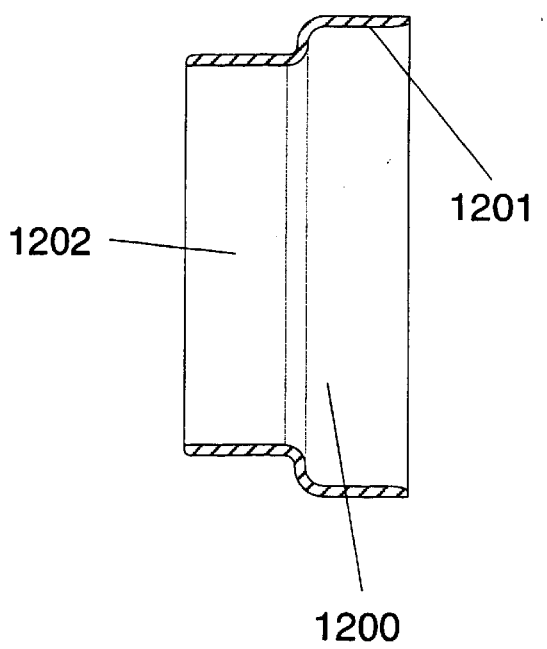
Figure 6C:
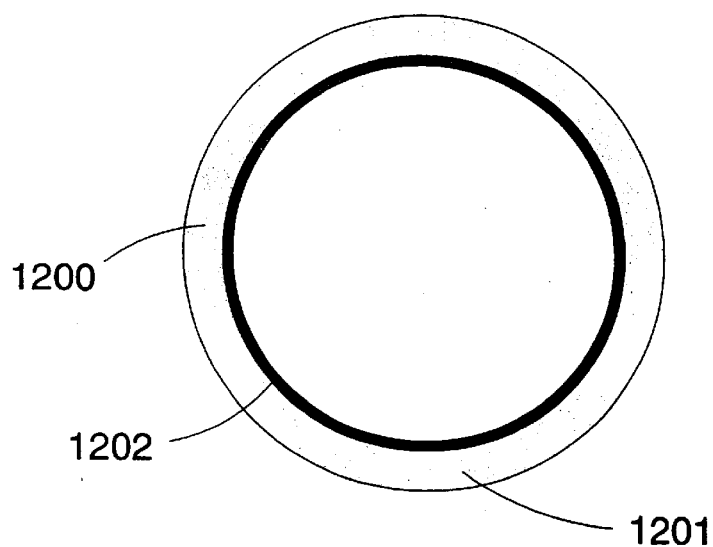
Figure 7A:
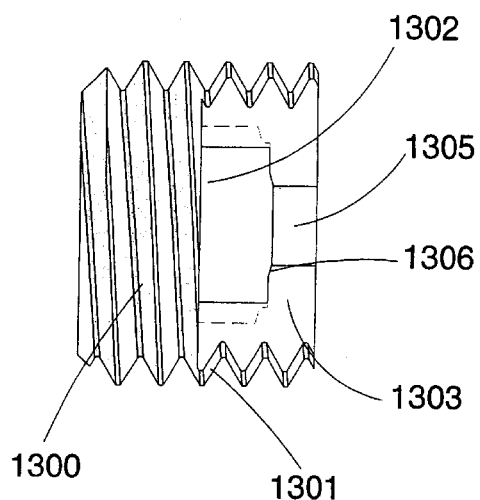
FIGS. 7a–d illustrate the threaded valve stem guide of a needle-less injector in accordance with an embodiment of the instant invention.
Figure 7B:
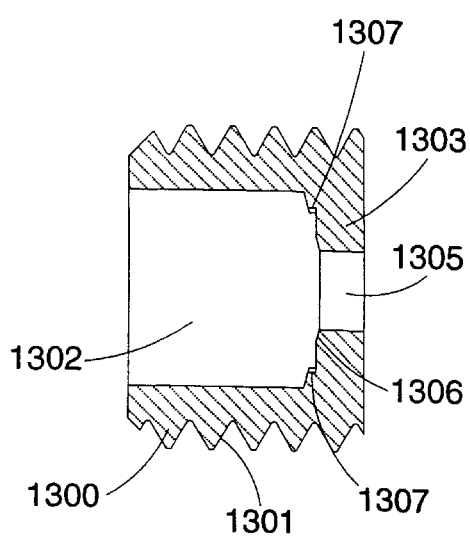
Figure 7C:
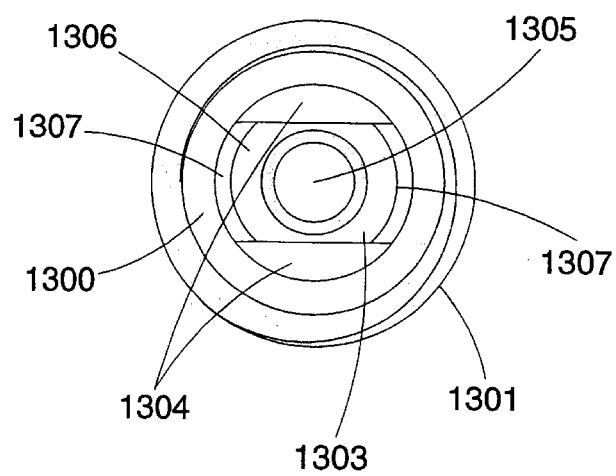
Figure 7D:
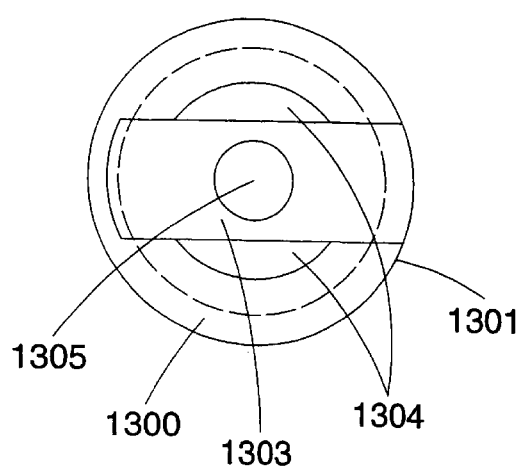

The closing ferrule 1200 is shown in FIG. 6 prior to its distal portion 1201 being mechanically bent around the closing rim 1101 and closing ridge 1006. The proximate portion 1202 of the closing ferrule 1200 is of substantially the same diameter as the exterior of the valve body 1100, such that bending the distal portion mechanically couples the valve body 1100 to the engine housing 1000. In FIG. 1b, the distal portion 1201 of the closing ferrule 1200 is shown in the bent state. The valve body 1000 preferably has a depression 1102 around its circumference adapted to fit a gasket 1103 (shown in FIG. 1a). The gasket 1103 helps ensure that an airtight seal is maintained between the interior of the engine housing 1000 which contains the gas and the local atmosphere.

Figure 10A:
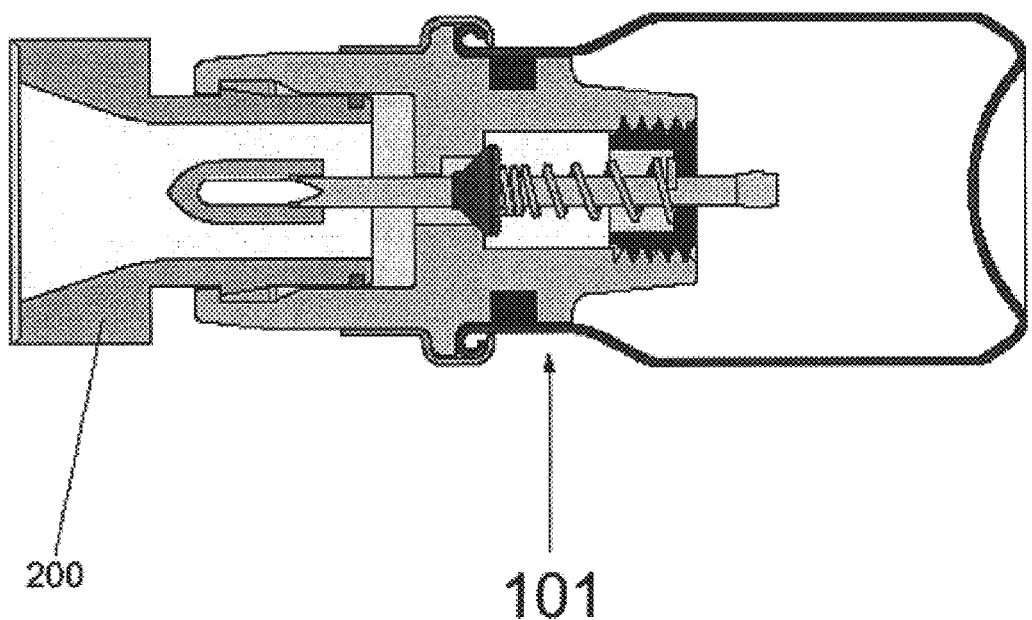
FIGS. 10a–b illustrate an engine with a valve operably interacting with another device, in accordance with an embodiment of the instant invention.
Figure 10B:
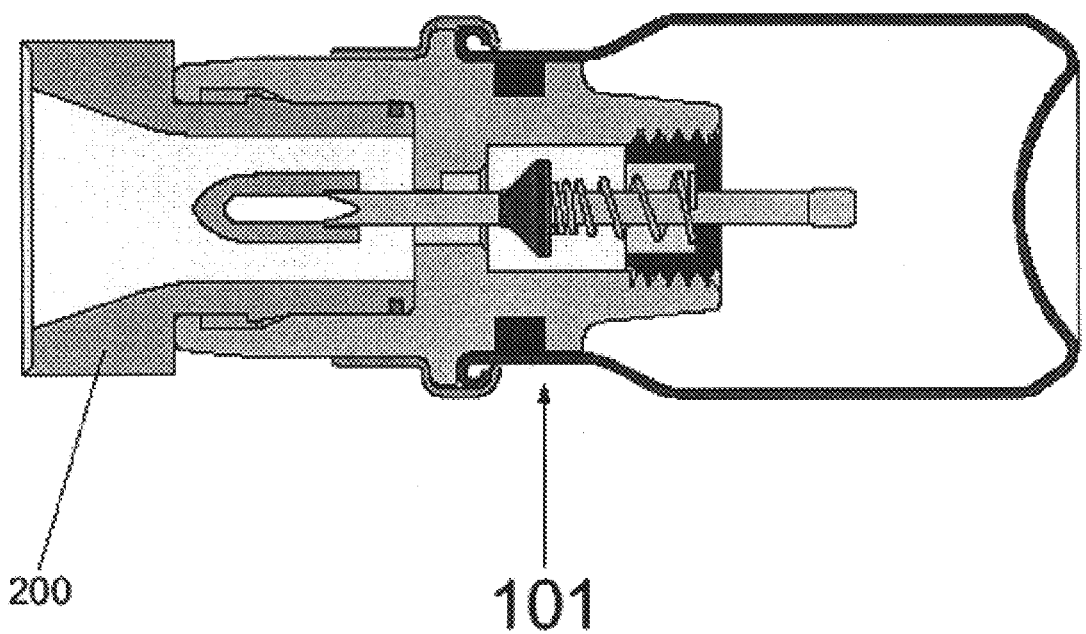

Referring to FIG. 5, the interior of the valve body 1100 is preferably hollow and comprised of several distinct portions. The distal interior portion 1104 of the valve body 1100 may contain a screw thread engagement 1105, preferably extending from the distal end of the valve body 1100 to the distal end of a first axial cavity 1106. The first axial cavity 1106 may be bounded on its proximate end by a shoulder 1107 that separates this first axial cavity 1106 from a second axial cavity 1108, which is preferably of smaller diameter than the first axial cavity 1106. In preferred embodiments, the shoulder 1107 is an angled edge. Also in preferred embodiments, at least one valve stem guide 1109 protrudes from the wall of the second axial cavity 1108. In a most preferred embodiment, there are at least three such valve stem guides 1109 that serve to substantially prevent the valve stem 1400 from moving in any direction other than along the central axis of the engine during an operation thereof In one embodiment of the present invention, the proximate end of a chamber 1110 preferably has at least one grip 1111 extending therefrom. Preferably, the at least one grip 1111 locks around another suitable element of a needle-less injector or other device to which the engine is in operable contact, as the gripping element 1112 is situated on the interior side of the grip 1111. In alternative embodiments, however, the at least one grip 1111 may lock within another element as the gripping element 1112 may be disposed on the exterior side of the grip 1111. In most preferred embodiments, there are two grips 1111 disposed opposite one another each of which contains a gripping element 1112 situated on the interior side of the grip 1111. In these most preferred embodiments, the two grips 1111 are slid over and lock around a corresponding mechanical element of another device. The interlocking of grips 1111 with such a mechanical element may aid in mitigating the kickback associated with deploying the compressed gas stored in the engine assembly 101. An example of this feature is illustratively depicted in FIG. 10 which illustrates an engine with a valve 101 of the instant invention interacting with another device 200 (FIG. 10a depicts the engine with a valve 101 in a closed position and FIG. 10b depicts the engine with a valve 101 in an open position).

The valve body 1100 preferably further contains a threaded valve guide 1300, as depicted in FIG. 7. The threaded valve guide 1300 is preferably cylindrical in shape and threaded around its exterior wall 1301, such that it may be screwed into the distal interior portion 1104 of the valve body 1100 by interacting with the screw thread engagement 1105. Most preferably, the threading on the exterior wall 1301 of the threaded valve guide 1300 extends along the entirety of the exterior wall 1301 from the distal to the proximate end of the threaded valve guide 1300. The threaded valve guide 1300 may also contain a cylindrical interior cavity 1302 that is unobstructed at the proximate end. The distal end, however, is preferably partially covered with a valve stem guide pane 1303. The valve stem guide pane 1303 preferably provides at least one vent 1304 allowing gaseous communication between the interior cavity 1302 of the threaded valve guide 1300 and the hollow interior chamber 1003 of the engine housing 1000 at the distal end of the threaded valve guide 1300. Also preferably, the valve stem guide pane 1303 includes a hole 1305 at the central axis slightly larger in diameter than the valve stem 1400 that resides therein. Most preferably, the valve stem guide pane 1303 further includes a spring seat 1306 on its proximate surface that is comprised of at least one ridge 1307 that maintains the valve spring 1500 in proper position.

Figure 8A:
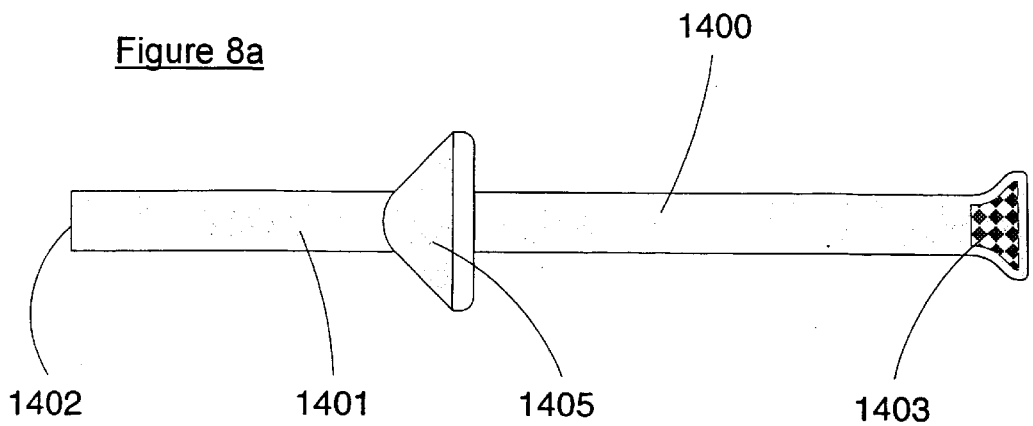
FIGS. 8a–c illustrate the valve stem of a needle-less injector in accordance with an embodiment of the instant invention.
Figure 8B:
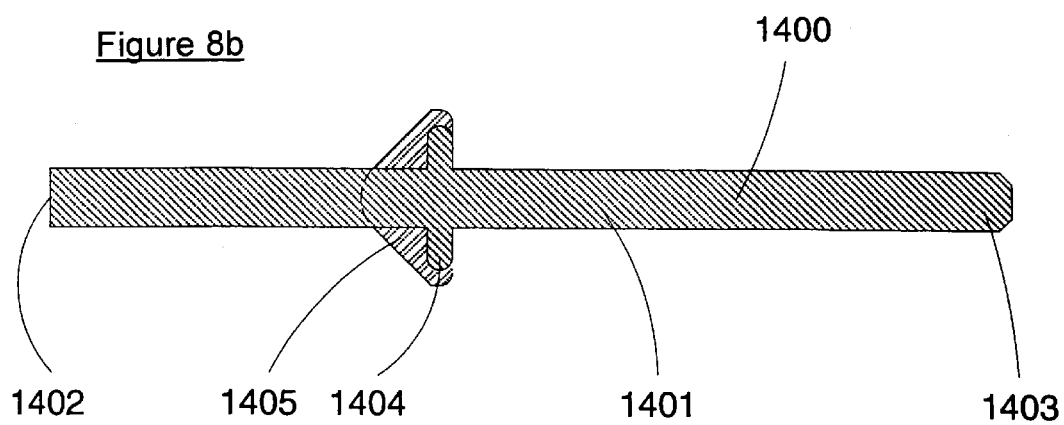
Figure 8C:
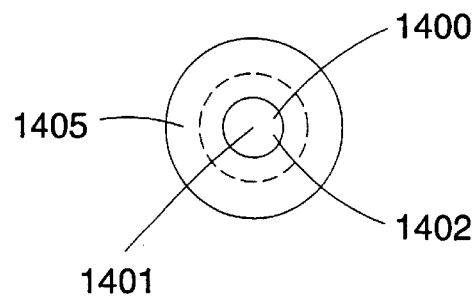

The valve body 1100 preferably further contains a valve stem 1400, as depicted in FIG. 8. The valve stem 1400 is preferably comprised of a substantially cylindrical rod 1401 having a proximate end 1402 which is flat and a distal end 1403 which is preferably pressed or hammer-forged. The distal end 1403 is shown after hammer-forging in FIG. 8aand prior to hammer-forged in FIG. 8b. Most preferably, there is also included a spring ridge 1404 that extends radially from the rod 1401, and a roughly conical valve head 1405 affixed to the proximate and exterior surfaces of the spring ridge 1404 as well as that portion of the rod 1401 immediately proximate to the spring ridge 1404. Most preferably, the valve head 1405 is comprised of a rubber material such as semi-permeable, silicon-based or butyl-based rubber that is sufficiently malleable for use in accordance with the engine. In most preferred embodiments, the angle between the proximate surface of the valve head 1405 and the central axis is substantially similar to the angle of the shoulder 1107 located between the first axial cavity 1106 and second axial cavity 1108 of the valve body 1100.

Figure 9A:
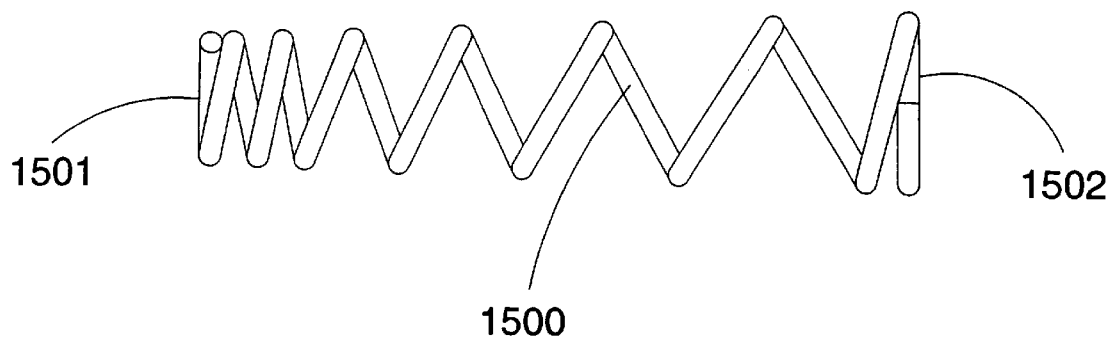
FIGS. 9a–b illustrate the valve spring of a needle-less injector in accordance with an embodiment of the instant invention.
Figure 9B:
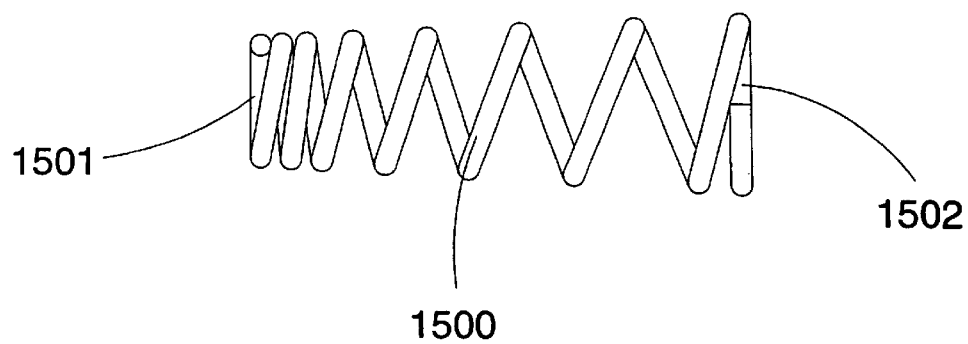

The valve body 1100 may further contain a valve spring 1500, as depicted in FIG. 9. The valve spring 1500 is preferably composed of wire and semi-conical in shape, wherein the proximate end 1501 is smaller in diameter than the distal end 1502. The proximate end 1501 of the valve spring 1500 preferably rests against the distal surface of the spring ridge 1404 on the valve stem 1400, while the distal end 1502 of the valve spring 1500 preferably rests against the proximate surface of the valve stem guide pane 1303 and is held in place radially by the spring seat 1306.

Figure 2:
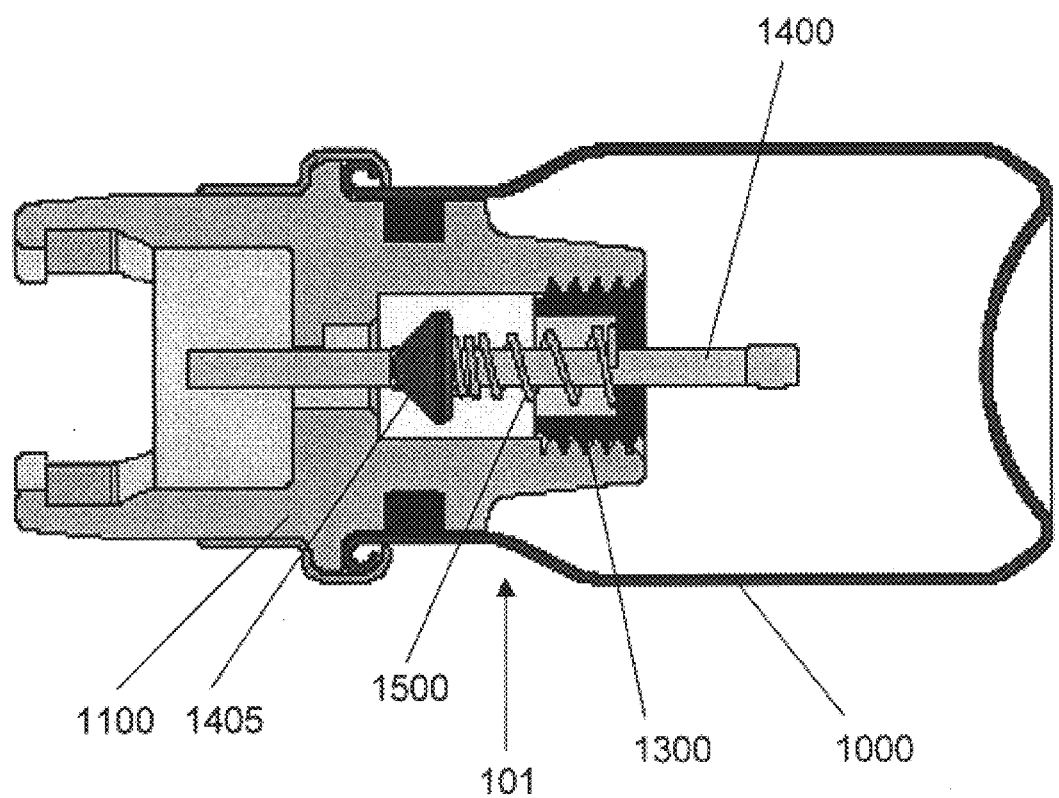
FIG. 2 illustrates a cross-sectional view of an engine with a valve in an open position in accordance with an embodiment of the instant invention.

Furthermore, the valve of the instant invention may be repeatedly opened and closed without being destroyed (FIGS. 1a and 2, respectively), thus it may be inspected for quality control determinations by opening and closing at least one time prior to the engine assembly 101 being filled with compressed gas.

Moreover, the engine and valve of the present invention may be readily scaled up or down to any desirable proportion without significant variation from the illustrative configurations set forth herein. Such configurations may be readily ascertained without undue experimentation. For instance, the engine and valve may be made to a substantially large size to function in conjunction with heavy-scale mechanical equipment. Alternatively, the engine and valve may be made to a substantially small size to operate along with micro-scale devices.

EXAMPLE 1

Filling an Engine that Includes a Valve with a Compressed Gas

An uncharged engine assembly includes a valve, and is not filled with compressed gas. The uncharged engine assembly is placed in a sealed, pressure-controlled environment, and the ambient pressure in the sealed environment is raised by the forced addition of $N_2$. The heightened ambient pressure forces the valve of the engine into the open position, owing to the heightened pressure being relatively greater than the initial pressure within the engine housing. After the ambient pressure and pressure within the engine housing equilibrate (i.e., the pressure in the environment is substantially equal to the pressure within the engine assembly), the spring included in the engine provides a force differential that pushes the valve into the closed position. The ambient pressure in the sealed environment is then lowered, and the engine is ready for use.

EXAMPLE 2

Operation of a Gas-Pressured Engine with a Valve

Prior to use, the engine assembly is checked for quality control purposes by opening and closing the valve, and thereafter the engine housing is filled with a suitable compressed gas. The circular depression on the engine housing is inspected to ensure no substantial deformation (i.e., the "pop-out" feature). When the valve stem is axially depressed relative to the remainder of the engine, the valve spring is compressed and the valve opens as the valve head is separated from the shoulder residing between the first and second axial cavities of the valve body. Compressed gas (previously stored in the engine housing, the interior cavity of the threaded valve guide and the first axial cavity of the valve body) may then rush through the gap created between the valve head and the shoulder. The gas rushes through the second axial cavity, past the valve stem guides, through the chamber and out the proximate end of the engine assembly.

While the description above refers to particular embodiments of the present invention, it should be readily apparent to people of ordinary skill in the art that a number of modifications may be made without departing from the spirit thereof The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. An engine comprising:
    an engine housing to contain a compressed gas, said engine housing including an engine housing opening; and
    a valve traversing said engine housing opening, said valve including:
        a valve opening;
        a valve stem;
        a valve head configured to obstruct the passage of a compressed gas through said valve opening when said valve is in a closed position, said valve head being affixed to said valve stem;
        a valve guide to maintain said valve stem in proper alignment with said valve opening, said valve guide further including a valve stem guide pane with a hole configured therein, said valve stem guide pane being configured perpendicularly to said valve stem, and said valve stem being slidably disposed within said hole; and
        a spring disposed between said valve head at a first spring end and said valve stem guide pane at a second spring end, said valve stem being slidably disposed within said spring.

2. The engine of claim 1, wherein said engine housing further includes a first portion terminating at one end at said engine housing opening.

3. The engine of claim 2, wherein said valve further includes an exterior valve surface.

4. The engine of claim 3, wherein said exterior valve surface resides within said first portion of said engine housing.

5. The engine of claim 4, said engine further including a gasket configured between said exterior valve surface and said first portion of said engine housing.

6. The engine of claim 5, wherein said exterior valve surface further includes a circumferential depression, and said gasket is disposed within said circumferential depression.

7. The engine of claim 3, wherein said first portion of said engine housing and said exterior valve surface are substantially cylindrical.

8. The engine of claim 3, wherein said valve further includes a closing rim disposed circumferentially about an exterior of said valve, and said exterior valve surface terminates at one end at said closing rim.

9. The engine of claim 8, wherein said engine housing further includes a closing ridge disposed circumferentially about said engine housing opening.

10. The engine of claim 9, said engine further including a closing ferrule to operably engage said closing rim and said closing ridge, and to maintain said closing rim and said closing ridge in a fixed position relative to one another.

11. The engine of claim 2, wherein said engine housing further includes a second portion configured between said first portion and an end of said engine housing.

12. The engine of claim 11, wherein said end of said engine housing further includes a depression to substantially deform when an internal pressure of said engine housing surpasses a pressure threshold.

13. The engine of claim 1, wherein said valve stem further includes an exterior valve stem portion that resides exterior to said valve opening.

14. The engine of claim 13, wherein said valve opens upon an application of a force to said exterior valve stem portion, wherein at least a component of said force is directed along a longitudinal axis of said valve stem.

15. The engine of claim 1, wherein said valve further includes an axial cavity partially defined by an interior surface of said valve.

16. The engine of claim 15, wherein said valve further includes at least one valve stem guide protruding from said axial cavity to substantially prevent said valve stem from moving in any direction other than transverse to said valve opening.

17. The engine of claim 16, wherein said valve further includes three valve stem guides, said three valve stem guides being disposed equidistant from one another about said axial cavity.

18. The engine of claim 15, wherein said axial cavity terminates at one end at said valve opening and at an opposing end at a shoulder, said shoulder being configured to contact said valve head when said valve is in said closed position.

19. The engine of claim 18, wherein said shoulder and said valve head are configured to contact one another in a manner that provides a substantially airtight seal therebetween.

20. The engine of claim 19, wherein said valve head is comprised of a material selected from the group consisting of silicon-based rubber and butyl-based rubber.

21. The engine of claim 15, wherein said valve further includes an additional axial cavity configured between said axial cavity and a valve guide end of said valve.

22. The engine of claim 21, wherein said valve further includes a segment of interior screw threading configured between said additional axial cavity and said valve guide end of said valve.

23. The engine of claim 22, wherein said valve guide further includes a segment of exterior screw threading to operably interact with said interior screw threading to attach said valve guide to said valve.

24. The engine of claim 1, wherein said valve further includes at least one vent configured between said valve stem guide pane and said valve guide to provide gaseous communication between said engine housing and an exterior of said engine.

25. The engine of claim 24, wherein said valve stem further includes a ridge configured circumferentially about said valve stem, said valve head being affixed to said ridge.

26. The engine of claim 1, wherein said first spring end includes a smaller diameter than said second spring end.

27. The engine of claim 1, wherein said valve stem further includes a pressed or hammer-forged end configured on an opposite side of said valve stem guide pane from said valve head.

28. The engine of claim 1, wherein said valve is capable of being repeatedly opened.

29. The engine of claim 1, wherein said valve further includes at least one grip to engage a device with which said engine operates, said at least one grip extending from that end of said valve through which a compressed gas is capable of escaping when said valve is in an open position, said at least one grip further including a gripping element adapted to lockingly engage with said device.

30. The engine of claim 1, wherein said engine is used in conjunction with a needle-less injector.

31. An engine comprising:
   an engine housing to contain a compressed gas, said engine housing including an engine housing opening; and
   a valve traversing said engine housing opening, said valve including:
      a valve opening;
      a valve stem;
      a valve head to obstruct the passage of a compressed gas through said valve opening when said valve is in a closed position, said valve head being affixed to said valve stem;
      a valve guide to maintain said valve stem in proper alignment with said valve opening; and
      at least one grip adapted to engage a device with which said engine operates, said at least one grip extending from that end of said valve through which a compressed gas is capable of escaping when said valve is in an open position, said at least one grip further including a gripping element adapted to lockingly engage with said device.

32. The engine of claim 31, wherein said engine housing further includes a first portion terminating at one end at said engine housing opening.

33. The engine of claim 32, wherein said valve further includes an exterior valve surface.

34. The engine of claim 33, wherein said exterior valve surface resides within said first portion of said engine housing.

35. The engine of claim 34, wherein said engine further including a gasket configured between said exterior valve surface and said first portion of said engine housing.

36. The engine of claim 35, wherein said exterior valve surface further includes a circumferential depression, and said gasket is disposed within said circumferential depression.

37. The engine of claim 33, wherein said first portion of said engine housing and said exterior valve surface are substantially cylindrical.

38. The engine of claim 33, wherein said valve further includes a closing rim disposed circumferentially about an exterior of said valve, and said exterior valve surface terminates at one end at said closing rim.

39. The engine of claim 38, wherein said engine housing further includes a closing ridge disposed circumferentially about said engine housing opening.

40. The engine of claim 39, said engine further including a closing ferrule to operably engage said closing rim and said closing ridge, and to maintain said closing rim and said closing ridge in a fixed position relative to one another.

41. The engine of claim 32, wherein said engine housing further includes a second portion configured between said first portion and an end of said engine housing.

42. The engine of claim 41, wherein said end of said engine housing further includes a depression to substantially deform when an internal pressure of said engine housing surpasses a pressure threshold.

43. The engine of claim 31, wherein said valve stem further includes an exterior valve stem portion that resides exterior to said valve opening.

44. The engine of claim 43, wherein said valve opens upon an application of a force to said exterior valve stem portion, wherein at least a component of said force is directed along a longitudinal axis of said valve stem.

45. The engine of claim 31, wherein said valve further includes an axial cavity partially defined by an interior surface of said valve.

46. The engine of claim 45, wherein said valve further includes at least one valve stem guide protruding from said axial cavity to substantially prevent said valve stem from moving in any direction other than transverse to said valve opening.

47. The engine of claim 46, wherein said valve further includes three valve stem guides, said three valve stem guides being disposed equidistant from one another about said axial cavity.

48. The engine of claim 45, wherein said axial cavity terminates at one end at said valve opening and at an opposing end at a shoulder, said shoulder being configured to contact said valve head when said valve is in said closed position.

49. The engine of claim 48, wherein said shoulder and said valve head are configured to contact one another in a manner that provides a substantially airtight seal therebetween.

50. The engine of claim 49, wherein said valve head is comprised of a material selected from the group consisting of silicon-based rubber and butyl-based rubber.

51. The engine of claim 45, wherein said valve further includes an additional axial cavity configured between said axial cavity and a valve guide end of said valve.

52. The engine of claim 51, wherein said valve further includes a segment of interior screw threading configured between said additional axial cavity and said valve guide end of said valve.

53. The engine of claim 52, wherein said valve guide further includes a segment of exterior screw threading to operably interact with said interior screw threading to attach said valve guide to said valve.

54. The engine of claim 31, wherein said valve guide further includes a valve stem guide pane with a hole configured therein, said valve stem guide pane being configured perpendicularly to said valve stem, and said valve stem being slidably disposed within said hole.

55. The engine of claim 54, wherein said valve further includes at least one vent configured between said valve stem guide pane and said valve guide to provide gaseous communication between said engine housing and an exterior of said engine.

56. The engine of claim 55, wherein said valve stem further includes a ridge configured circumferentially about said valve stem, said valve head being affixed to said ridge.

57. The engine of claim 56, wherein said valve further includes a spring disposed between said ridge at a first spring end and said valve stem guide pane at a second spring end.

58. The engine of claim 57, wherein said first spring end includes a smaller diameter than said second spring end.

59. The engine of claim 54, wherein said valve stem further includes a flattened end configured on an opposite side of said valve stem guide pane from said valve head.

60. The engine of claim 31, wherein said valve is capable of being repeatedly opened.

61. The engine of claim 31, wherein said engine is used in conjunction with a needle-less injector.

62. A method for determining whether an engine housing is critically overcharged comprising:
    providing an engine housing including:
        a first end that further includes a depression capable of substantially deforming when an internal pressure of said engine housing surpasses a pressure threshold, and
        a second end operably coupled to a valve, said valve including:
            a valve opening,
            a valve stem,
            a valve head configured to obstruct the passage of a compressed gas through said valve opening when said valve is in a closed position, said valve head being affixed to said valve stem,
            a valve guide to maintain said valve stem in alignment with said valve opening, said valve guide further including a valve stem guide pane with a hole configured therein, said valve stem guide pane being configured perpendicularly to said valve stem, and said valve stem being slidably disposed within said hole, and
            a spring disposed between said valve head at a first spring end and said valve stem guide pane at a second spring end, said valve stem being slidably disposed within said spring;
    filling said engine housing with a compressed gas;
    inspecting said depression for a substantial deformation; and
    determining that said engine housing is critically overcharged if a substantial deformation is found on said first end.

63. The method of claim 62, wherein said engine housing is used in conjunction with a needle-less injector.

64. The method of claim 62, said method being implemented as at least a part of a manufacturing quality control scheme.

65. A method of filling an engine with a compressed gas comprising:
    providing an engine including:
        an engine housing to contain a compressed gas, said engine housing including an engine housing opening, and
        a valve traversing said engine housing opening, said valve including:
            a valve opening,
            a valve stem,
            a valve head configured to obstruct the passage of a compressed gas through said valve opening when said valve is in a closed position, said valve head being affixed to said valve stem,
            a valve guide to maintain said valve stem in alignment with said valve opening, said valve guide further including a valve stem guide pane with a hole configured therein, said valve stem guide pane being configured perpendicularly to said valve stem, and said valve stem being slidably disposed within said hole, and
            a spring disposed between said valve head at a first spring end and said valve stem guide pane at a second spring end, said valve stem being slidably disposed within said spring;
    placing said engine within a pressure-controlled environment;
    raising a pressure level in said pressure-controlled environment to a raised pressure level; and
    allowing a pressure within said engine to equilibrate with said raised pressure level.

66. The method of claim 65, wherein said valve further includes a spring to push said valve into a closed position once said pressure within said engine equilibrates with said raised pressure level.

67. The method of claim 65, wherein raising a pressure level includes forcing a gas into said pressure-controlled environment.

68. The method of claim 67, wherein said gas is selected from the group consisting of air, carbon dioxide ($CO_2$), nitrogen ($N_2$) and inert gases.

69. The method of claim 65, wherein allowing a pressure within said engine to equilibrate with said raised pressure level further includes waiting for said valve to move into a closed position.

70. The method of claim 65, further including using said engine in conjunction with a needle-less injector.

71. A method for determining whether an engine housing is critically overcharged comprising:
    providing an engine housing including:
        a first end that further includes a depression capable of substantially deforming when an internal pressure of said engine housing surpasses a pressure threshold, and
        a second end operably coupled to a valve, said valve including:
            a valve opening,
            a valve stem,
            a valve head to obstruct the passage of a compressed gas through said valve opening when said valve is in a closed position, said valve head being affixed to said valve stem,
            a valve guide to maintain said valve stem in alignment with said valve opening, and at least one grip adapted to engage a device with which said engine operates, said at least one grip extending from that end of said valve through which a gas is capable of escaping when said valve is in an open position, said at least one grip further including
a gripping element adapted to lockingly engage with said device;

filling said engine housing with a compressed gas;

inspecting said depression for a substantial deformation; and determining that said engine housing is critically overcharged if a substantial deformation is found on said first end.

72. The method of claim 71, wherein said engine housing is used in conjunction with a needle-less injector.

73. The method of claim 71, said method being implemented as at least a part of a manufacturing quality control scheme.

74. A method of filling an engine with a compressed gas comprising:

providing an engine including:
an engine housing to contain a compressed gas, said engine housing including an engine housing opening, and
a valve traversing said engine housing opening, said valve including:
a valve opening,
a valve stem,
a valve head to obstruct the passage of a compressed gas through said valve opening when said valve is in a closed position, said valve head being affixed to said valve stem,
a valve guide to maintain said valve stem in alignment with said valve opening, and
at least one grip adapted to engage a device with which said engine operates, said at least one grip extending from that end of said valve through which a gas is capable of escaping when said valve is in an open position, said at least one grip further including a gripping element adapted to lockingly engage with said device;

placing said engine within a pressure-controlled environment;

raising a pressure level in said pressure-controlled environment to a raised pressure level; and allowing a pressure within said engine to equilibrate with said raised pressure level.

75. The method of claim 74, wherein said valve further includes a spring to push said valve into a closed position once said pressure within said engine equilibrates with said raised pressure level.

76. The method of claim 74, wherein raising a pressure level includes forcing a gas into said pressure-controlled environment.

77. The method of claim 76, wherein said gas is selected from the group consisting of air, carbon dioxide ($CO_2$), nitrogen ($N_2$) and inert gases.

78. The method of claim 74, wherein allowing a pressure within said engine to equilibrate with said raised pressure level further includes waiting for said valve to move into a closed position.

79. The method of claim 74, further including using said engine in conjunction with a needle-less injector.

* * * * *